United States Patent [19]
Knapp

[11] Patent Number: 5,672,316
[45] Date of Patent: Sep. 30, 1997

[54] MICROWAVE-HEATABLE PRESSURE REACTOR

[76] Inventor: Gunter Knapp, Sorgerweig 16, A-8047 Graz, Austria

[21] Appl. No.: 399,754

[22] Filed: Mar. 7, 1995

[30] Foreign Application Priority Data

Mar. 11, 1994 [AT] Austria .................................. 532/94

[51] Int. Cl.⁶ .................................................. A61L 2/00
[52] U.S. Cl. .................. 422/21; 422/106; 422/129; 422/186; 422/208; 422/242; 422/307; 422/905; 423/659
[58] Field of Search .......................... 422/21, 41, 106, 422/129, 186, 199, 208, 242, 307, 905; 423/659, 245.1, 245.2

[56] References Cited

U.S. PATENT DOCUMENTS

| | | | |
|---|---|---|---|
| Re. 30,780 | 10/1981 | Stenstrom | 422/21 X |
| 3,706,631 | 12/1972 | Falk | 422/21 |
| 4,839,142 | 6/1989 | Charm | 422/21 |
| 4,975,246 | 12/1990 | Charm | 422/21 |
| 4,980,039 | 12/1990 | Aysola et al. | 422/21 X |
| 5,215,715 | 6/1993 | Haswell et al. | 422/81 |
| 5,246,674 | 9/1993 | Katschnig et al. | 422/302 |
| 5,314,664 | 5/1994 | Sperling et al. | 422/78 |
| 5,340,536 | 8/1994 | Datar et al. | 422/23 |
| 5,389,335 | 2/1995 | Charm et al. | 422/21 |
| 5,403,564 | 4/1995 | Katschnig et al. | 422/307 |

FOREIGN PATENT DOCUMENTS

| | | |
|---|---|---|
| 3919601 | 12/1989 | Germany. |
| 4114525 | 8/1992 | Germany. |
| 4108766 | 9/1992 | Germany. |
| 4300957 | 7/1994 | Germany. |
| 4412887 | 10/1995 | Germany. |
| 4413426 | 10/1995 | Germany. |

OTHER PUBLICATIONS

Determination of total phosphorus in waters with amperometric detection by coupling of flow–injection analysis with continuous microwave oven digestion, S. Hinkamp et al., Analytica Chimica Acta. 236 (1990) 345–350 Elsvier Science Publ B.V., Amsterdam, pp. 345–350.

Experiences With On–Line Microwave Digestion In Flow––Injection Atomic Absorption Spectrometry, D.L. Tsalev et al., Colloquium Atomspektrometrische Spurenanalytik, pp. 349–366, 1991.

Atomic Absorption Spectrometric Analysis of Solids With On–Line Microwave–assisted Digestion, V. Carbonell et al., Journal of Analytical Atomic Spectrometry, Oct. 1992, vol. 7, pp. 1085–1089.

Determination of lead in Biological Materials by Microwave–assisted Mineralization and Flow Injection Electrothermal Atomic Absorption Spectometry, J.L. Burguera, et al., Journal of Analytical Atomic Spectrometry, Mar. 1993, vol. 8, pp. 235–241.

Kopplung von Mikrowellen–aufschluss und Hydrid–AAS, Andreas Meyer et al., Spektroskopie, Labor Praxis—Apr. 1993, pp. 44–48.

On–line Microwave Digestion of Slurry Samples With Direct Flame Atomic Abosorption Spectrometric Elemental Detection, Stephen J. Haswell et al., Analyst, Feb. 1992, vol. 117, pp. 117–120.

Rapid Stopped–flow Microwave Digestion System, Vassili Karanassios, et al., Journal Of Analytical Atomic Spectromety, Sep. 1991, vol. 6, pp. 457–463.

*Primary Examiner*—Robert J. Warden
*Assistant Examiner*—Krisanne M. Thornton
*Attorney, Agent, or Firm*—Steinberg, Raskin & Davidson, P.C.

[57] ABSTRACT

A microwave-heatable pressure reactor is provided for continuous or discontinuous treatment of liquid. The liquid is conveyed by means of a high-pressure pump in a pipeline which extends into a microwave-heatable zone of the pressure container into which it finally lets out through the free opening with a volume of pipe sufficient for the treatment of a desired quantity of liquid.

20 Claims, 1 Drawing Sheet

MICROWAVE-HEATABLE PRESSURE REACTOR

BACKGROUND OF THE INVENTION

The present invention relates to a microwave-heatable pressure reactor used to heat liquids. The reactor includes a container, microwave means for generating a microwave field in the container, a pipeline to carry liquid to be heated, and conveying means to convey the liquid through the pipeline and into the container. At least a segment of the length of the pipeline consists of a microwave-transparent material in which the liquid can be heated in a microwave field.

The present invention also relates to a process for sterilizing liquids and a process for carrying out wet chemical reactions involving a portion, i.e., liquids or suspensions, and a reagent.

Heating liquid streams in a microwave field has become very important in sterilizing liquids and to carry out wet chemical reactions. In devices in which such processes are applied, the liquid is conveyed through microwave-transparent hoses or pipes located in a microwave field by means of a pump. Also, in devices of this type, the hoses or pipes which are made of a synthetic material are normally located in a container which is itself made in form of a microwave oven.

When the liquid freely emerges from the hose or pipe system after passing through the microwave field, the pressure inside the pipe is approximately equal to the prevailing outside pressure so that the maximum attainable temperature is the boiling temperature of the liquid in use at atmospheric pressure. Such a process is especially well-suited for continuous processing, often called "continuous flow".

A number of such arrangements are described in the prior art, e.g., in a paper by S. Hinkamp and G. Schwedt, Anal. Chim. Acta, 236 (1990) 345; D. L. Tsalev, M. Sperling, B. Welz, 5th Colloquium "Atmospectrometric Spurenanalytik, B. Welz (publisher) and in a paper by V. Carbonell, A. Morales-Rubio, A. Salvador, M. de la Guardia, J. L. Burguera, M. Burguera, JAAS 7 (1992) 1085; J. L. Burguera, M. Burguera, JAAS 8 (1993 ) 235 and A. Meyer, G. Schwedt, Labor Praxis —April 1993, 44.

However, it is a disadvantage of these prior art arrangements that the maximum temperatures of the liquid which can be attained in the microwave field is often insufficient in order to allow sterilization or chemical reactions to take place to completion. For this reason, devices were developed which make it possible to heat the liquid under pressure in the pipe system.

This is done for example by means of suitable restrictors or valve systems at the output of the hose or pipe system (see, e.g., S. J. Haswell, D. Barclay, Analyst 117 (1992) 117 and U.S. Pat. No. 5,215,715).

Another process for sterilizing liquids and performing wet chemical reactions consists in installing a stop valve at the input and at the output of the hose or pipe system. When the system has been filled with the liquid to be heated the conveying pump is switched off, the two stop valves are closed and the microwave heating system is switched on. Since the system is closed during heating, pressure builds up accordingly.

Upon completion of the heating cycle, the stop valves are opened, the conveying pump is switched on and the liquid in the pipe reactor is replaced by new liquid. This process is conventionally referred to as the "stopped-flow system" and is described in a paper by V. Karanassios, F. H. Li, B. Liu, E. D. Salin, JAAS 6 (1991), S 457.

By increasing the pressure in the closed system, the liquid can be brought to the correspondingly higher temperatures. It is a drawback though that in such a process, limits for pressure or temperature increase which are due to mechanical loading capacity of the hose or pipe material are however soon reached. Only about 10 bar overpressure can be handled with TEFLON hoses or pipes (TEFLON is a registered trademark of Du Pont). Teflon™ is one suitable material used to carry a liquid through a microwave field.

OBJECTS AND SUMMARY OF THE INVENTION

It is therefore an object of the instant invention to develop a device in which the advantages of microwave heating in microwave-tarnsparent hose or pipe systems can also be used at pressures such as would normally exceed the capacity of such systems. For many wet chemical reactions, in particular the removal of organic material by means of oxidizing acids such as nitric acid, temperatures at which much higher steam pressures than 10 bar occur are needed. It is desirable in this case to operate at pressures of up to approximately 100 bar.

It is another object to provide a new and improved apparatus and process for heating liquids in a microwave field in which the disadvantages of the prior art arrangements and processes are substantially eliminated.

These objects and others are attained by a pressure reactor comprising a container which is made in form of a pressure container with means for building up pressure in the interior of the container, i.e., associated container pressurizing means, and whereby an outlet opening is provided in the lower area of the container with means for regulating the liquid through-flow. The container is made, at least in one area, of a microwave-transparent material and a pipeline, through which a liquid is carried into the container, is pressure-tight inside the container and preferably enters through a free opening of the pipeline into the pressurized interior space of the container. At least one segment of the pipeline situated in the container is made of a microwave-transparent material such that the microwave-transparent segment (heating area) of the pipeline is located in the microwave-transparent section of the container. The pipeline may of course extend through the container without releasing the liquid therein.

In this manner, a simple and elegant arrangement in accordance with the invention may consist in heating the liquid in the microwave-heatable pipe system, using TEFLON™ at temperatures of up to about 260° C. and avoiding the application of a pressure load to the pipe system in the interior of the container. The pressure load to the pipe system is avoided as a result of the presence of an equilibrium state between the pressure inside the container and the pressure in the pipeline, both of which are situated in the microwave field. Other than the temperature load, no additional mechanical stress acts upon the pipe system.

To increase the gas pressure inside the container, an inert gas, in particular nitrogen coming from a nitrogen bomb, is used, whereby the inert gas is preferably conveyed via a pressure gas line into the inside of the container.

When carrying out wet chemical reactions it may be desirable to define the space of the heating area precisely. This can be done in different manners. The container may be made of any desired, pressure-resistant material which is inert to the substances used, whereby windows made of a microwave-transparent material are incorporated into the mantle or sides of the container in order to engage or disengage the microwave field. The pressure container may however also be made entirely of a microwave-transparent material, whereby the microwave field is suitably limited by appropriate blinds (microwave restricting means) outside or inside the container. It is also possible to use a microwave generator which produces a microwave field that is already well collimated. In the cases mentioned, it is possible but not required to make the entire segment of the pipeline located inside the container of a microwave-transparent material. If the space occupied by the microwave field within the container is however poorly defined, it is also possible to make the pipeline of a microwave-transparent material only within a certain area and determine the effective range of the microwave field to align therewith.

In order to obtain as wide an effective range of the microwave field as possible while keeping the dimensions of the pressure reactor as small as possible, the microwave-transparent heating area of the pipeline may be extended in the microwave field, i.e., more than a straight line between the inlet of the pipeline into the container and the end of the pipeline through which the liquid enters into the container. Such an extension is possible by means of a meandering course of the pipeline. In one preferred embodiment, the pipeline is constructed in the form of a pipe coil in the area of the microwave field.

The microwave-transparent container material selected is preferably quartz, polytetrafluorethylane (PTFE) or polyethylenketone (PEK). The microwave-transparent area of the pipeline is preferably made of polytetrafluoroethylene (PTFE) or perfluoralkoxy (PFA). The pipeline may be made of a different material outside and inside the container. For example, the pipeline outside the container may be constructed of special steel and inside the container of PTFE. It is however also possible for the entire pipeline to be constructed of PTFE and to be provided outside the container with a special-steel casing to reinforce it against the high internal pressure in the line.

The pressure reactor is advantageously provided with means to cool the liquid in the microwave field. This cooling system may be installed in the area of the container outlet opening for the cooling of the liquid accumulated there, in the area of the pipeline between the heating zone located in the microwave field and the free opening of the line inside the container, or in the area of means for regulating the liquid flow. The cooling means serve on the one hand to prevent an evaporation or atomization of the heated liquid as it emerges from the pipeline or from the container opening. On the other hand, if cooling means are installed immediately downstream of the microwave field on the pipeline, the reaction conditions can have well-defined parameters because the reaction mixture is cooled immediately upon leaving the microwave fields and a continuation of the reaction is prevented.

The opening through which the pipeline lets out into the interior of the container can advantageously tapered, so that rising of bubbles within the line is prevented.

Liquid is conveyed through the pipeline only when the pressure produced by the conveying means is greater than the pressure inside the container. Therefore, a high-pressure pump is preferably connected to the pipeline to pump the liquid to be treated via the heating zone into the container. This most basic embodiment of the device in accordance with the invention is used for example for the sterilization of liquids or to carry out wet chemical reactions when the reaction partner is already available in mixed form. A portion in form of a liquid or a suspension can however also be mixed with one or more reagents by means of a multichannel pump or several individual pumps and can be conveyed through the pipeline via a portion loop and a portion input valve by means of an additional conveying fluid. Other inlet flow regulation means may also be used.

The lower sector of the pressure container is preferably tapered, with the container outlet opening being located at the lowest point of the tapering sector. Preferably the tapering is in form of a funnel. The design of the container bottom according to the invention effectively prevents adhesion of residues and this results in particular in increased precision of possible analysis which may follow.

The pipeline is advantageously extended beyond the heating zone and projects into the tapered zone of the container. At higher output speeds of the liquid from the pipeline a suction effect, such as is known with gas jet pumps, is produced, and in the present case this also contributes to a reduction of residue, in addition counteracting possible clogging of the container outlet opening.

In another embodiment, the container outlet opening can also be extended by a drain pipe. The flow regulation means may be located in the outlet opening of the container or in the drain pipe. The flow regulation means may comprise a stop valve for example, by means of which the outlet opening can be closed off completely, this being especially advantageous for discontinuous operation. On the other hand, the regulating means may also comprise a restrictor by means of which a given flow amount can be set in continuous operation. Furthermore, reflux means may be provided at the container outlet opening to prevent the escape of gas from the container interior under pressure.

The pressure reactor is advantageously provided with means which prevent the treated liquid which has passed out of the pipeline, after passing through the microwave heating field, from rising inside the container to such an extent that it again comes within the effective range of the microwave field. It is therefore possible to provide a flow control in the drain pipe which indicates whether the drain coming out of the container is clogged, and which may switch off the conveying means and/or the microwave field if necessary. Inside the container, a level control can also be provided which switches off the conveying means and/or the microwave field when a given minimum level of treated liquid is reached in the container.

An important advantage realized by means of the pressure reactor in accordance with the invention over the known devices of this type operating under internal pressure consists in the fact that outside and inside pressures of the microwave-transparent pipe or hose system in the interior of the container are substantially equal so that comparatively very high pressures corresponding to the steam pressure curves of the liquids being treated can be used.

Under these conditions, absolutely constant pressure conditions apply to the pipe system containing the liquid and to the liquid to be treated itself during the most varied operating conditions, i.e. in continuous, discontinuous or "stopped flow" operation. This is very important for a uniform execution of the processes and thereby for good reproducibility of the chemical reactions. The reaction time may be selected within a wide range. Continuous-flow as well as stopped-flow operation is possible.

The instant invention also relates to a process to carry out wet chemical reactions using the pressure reactor according to the invention, whereby a certain amount of overpressure is produced in the container, the portion is mixed with at least one reagent, the reaction mixture is conveyed into the pressure container by means of conveying devices and possibly a conveying fluid, the reaction mixture is guided through a microwave field of defined dimensions and after being heated is allowed to flow out of the free opening of the pipeline into the interior of the container, the treated liquid being removed through the outlet opening. The process in accordance with the invention is also suited for the sterilization of liquids, for which the above-described mixing phase with a reagent may be omitted.

BRIEF DESCRIPTION OF THE DRAWING

The following drawing is illustrative of embodiments of the invention and is not meant to limit the scope of the invention as encompassed by the claims.

DETAILED DESCRIPTION OF THE INVENTION

Figure 1:
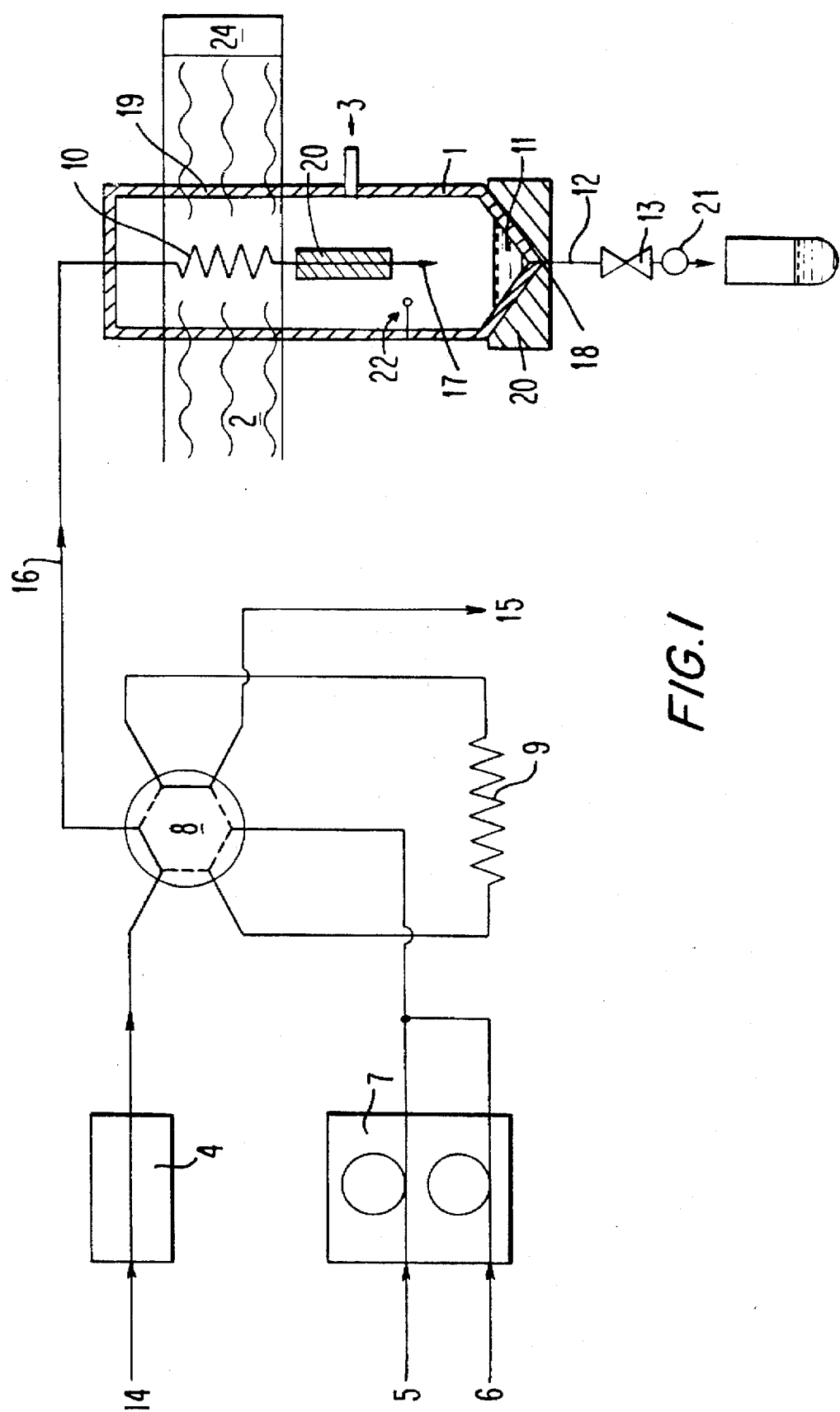
FIG. 1 shows a pressure reactor in accordance with the invention to sterilize liquids or carry out wet chemical reactions and in which the process in accordance with the invention may be applied.

In accordance with the invention, the pressure reactor comprises a pressure container 1 made of a microwave-transparent material. An upper section of the container 1 is located in a microwave field 2 which is generated by conventional microwave radiation generating means 24. The pressure container 1 may be either entirely microwave-transparent or only in a window-like area 19 thereof. The pressure container 1 is put under pressure or pressurized at the start of the operation via a gas line 3 using an inert gas, preferably nitrogen. The pressure applied by the build up of nitrogen in the container 1 may be as high as 100 bar. The portions are conveyed continuously to the pressure container 1, similarly as in high-pressure liquid chromatography. A high-pressure pump 4 continuously conveys a conveying fluid 14 through a pipeline 16 into the pressure container 1. If the apparatus is used to sterilize water, then the conveying fluid would be the water to be sterilized. A portion 5 and a reagent 6 are conveyed by means of pump 7 into a portion input valve or portion dosage device 8. When a portion loop 9 of the input valve 8 is full, the valve 8 reverses and the portion loop 9 lies within the high-pressure liquid stream of conveying fluid 14 coming from pump 4. Excess conveying fluid is removed through drain 15 from the portion dosage device.

The conveying fluid 14 then conveys the portion/reagent mixture through a microwave-transparent segment 10 of the pipeline 16, e.g. a coil made of TEFLON ™ hose, into the pressure container 1. The coil of the pipe system is located in the microwave field 2 where the temperature treatment of portion and reagent takes place. Following this, the mixture and the conveying fluid flow out of a free opening 17 of pipeline 16 into a lower sector of the pressure container 1. If necessary, cooling devices 20 to cool the treated liquid are provided before the opening 17 and/or in the lower sector of the pressure container. At the lowest point of the container, an outlet opening 18 followed by a line 12 is provided. The liquid 11 is drawn out of the pressure container 1 through outlet opening 18 and into line 12. The conveying of the liquid from the container 1 is ensured by the pressure gas in pressure container 1. The flow rate of the efflux liquid is set by means of an adjustable or fixed restrictor 13, or other suitable flow regulating means.

A flow control device 21, e.g. in form of bubble or drop counter, may be provided in line 12. Similarly, a level control 22 may be arranged in the interior of the container to monitor the level of the treated free liquid 11. Flow and level control may be connected to signalling devices which inform the user of any malfunction in operation. Similarly, the flow and level control devices may be connected directly to the high-pressure pump 4 or to the generator for the production of the microwave field 2 and switch these off in case of a malfunction. Regulation of the high-pressure pump 4 or of the microwave field 2 in function of flow or level of the liquid 11 may be desired under certain conditions and appropriate regulation means may be provided to control these units.

Even though the pressure container according to FIG. 1 is vertical, the invention is not limited thereto. The pressure container 1 may assume any angle or position allowing for the collection of the liquid in the lower sector of the container.

Instead of the restrictor 13, which allows for continuous portion processing, a stop valve allowing for discontinuous portion processing may also be used.

The gas pressure created in the pressure container 1 results in the desired increase of the boiling temperature in the hose 10, without constituting a mechanical load for the hose 10 because substantially the same pressure prevails inside and outside the hose system in the interior of the container 1.

In order to maintain this pressure equilibrium, the interior pressure of the container and the pressure in the portion lines must be coordinated.

The device according to the invention may be used for many different purposes of which a sterilization process for liquids and performing wet chemical reactions will be described.

1. Sterilization of liquids:

A liquid to be sterilized is pumped continuously into the pressure container 1 by means of the high-pressure pump 4, and there, in the area 10 of the pipe system 10, it is subjected to the influence of the microwaves 2 and is heated to a temperature at which sterilization occurs. The liquid is withdrawn at the lower reactor end via line 12, also in continuous operation. The input of portion 5 and reagent 6, in particular the portion pump 7 and the portion input valve 8 are omitted.

2. Carrying out wet chemical reactions:

The portion 5, consisting of liquids or suspensions, is mixed with one or more reagents by means of a multichannel pump or several individual pumps 7 and is conveyed into the portion input valve 8. This reaction mixture, together with the conveying fluid 14, is conveyed into the pressure container 1 by means of the high-pressure pump 4. This procedure is used, e.g., for the removal of organic material by means of oxidizing acids such as nitric acid.

Referring again to FIG. 1, the pressure container 1 has two zones. The upper zone is located in the microwave field. The portion is conveyed in this zone in a microwave-transparent hose or pipeline 10. The lower zone of the pressure container 1 is located outside the microwave field. In this zone, the liquid emerges from the input line and collects at the bottom of the container 1. From there, it is conveyed continuously out of the pressure container by means of the pressure gas via line 12 and restrictors 13.

The wet chemical reactions may be carried out continuously or discontinuously.

2.1 Continuous operation:

The high-pressure pump 4 conveys continuously. The liquid is therefore conveyed continuously through the microwave zone. The sojourn or delay time of the liquid in the microwave zone is determined by the flow rate of pump 4 and the volume of line 10.

2.2 Discontinuous operation:

The portion is conveyed by means of pump 4 from the portion input valve 8 into the microwave zone 10 of the pressure container. When the entire portion is in the microwave zone, the pump 4 is switched off for a given time period. In this manner, the portion is able to remain in the microwave zone for a reaction time of any desired duration. The line 12 may also be closed off by a stop valve if necessary.

The examples provided above are not meant to be exclusive. Many other variations of the present invention would be obvious to those skilled in the art, and are contemplated to be within the scope of the appended claims.

I claim:

1. A microwave-heatable pressure reactor for heating liquids, comprising
   a container having a pressurizable interior space, at least a part of said container comprising microwave-transparent material;
   means coupled to said container for pressurizing said interior space of said container;
   microwave heating means for generating a microwave field to be effective through said microwave-transparent part of said container to provide a heating zone in said interior space of said container;
   a pipeline for conveying a liquid from a source thereof into and at least partially through said container, at least a part of said pipeline situated in said container comprising microwave-transparent material and being arranged in said heating zone, said pipeline extending only partially through said container and having an outlet opening through which the liquid is released into said interior space of said container; and
   means for pumping the liquid from the source through the pipeline to the container and
   outlet means coupled to said container for removing liquid from said interior space of said container.

2. The pressure reactor of claim 1, wherein said container comprises a mantle having windows made of a microwave-transparent material to engage or disengage a microwave field with said container.

3. The pressure reactor of claim 1, wherein said container is made entirely of a microwave-transparent material.

4. The pressure reactor of claim 1, wherein said microwave-transparent part of said pipeline is extended so that it is not straight between an inlet of said pipeline into said container and said outlet opening of said pipeline through which the liquid is released from said pipeline.

5. The pressure reactor of claim 4, wherein said microwave-transparent part of said pipeline comprises a coiled pipe.

6. The pressure reactor of claim 1, further comprising cooling means for cooling the liquid, said cooling means being arranged to act upon the liquid in said pipeline after the liquid has passed through said microwave-transparent part of said pipeline.

7. The pressure reactor of claim 6, wherein said cooling means are coupled to said pipeline in an area thereof after said heating zone and before said outlet opening of said pipeline.

8. The pressure reactor of claim 1, wherein said pump means comprise a pump connected to said pipeline, said pump means pumping the liquid to be treated via said heating zone.

9. The pressure reactor of claim 8, further comprising means for regulating the inlet flow of liquid into said container, said inlet flow regulating means comprising a portion input valve coupled to said pipeline and a conveying fluid.

10. The pressure reactor of claim 1, wherein the microwave-transparent container material is selected from the group consisting of quartz, polytetrafluorethylane (PTFE) and polyethylenketone (PEK) and the microwave-transparent pipeline material is selected from the group consisting of polytetrafluoroethylene (PTFE) and perfluoralkoxy (PFA).

11. The pressure reactor of claim 1, further comprising outlet flow regulation means coupled to said outlet means for regulating an outlet flow of the liquid from said interior space of said container.

12. The pressure reactor of claim 11, wherein said container has a tapered lower sector and said outlet means comprise an outlet opening arranged at a lowest point of said tapered lower sector, said tapered lower sector comprising a funnel.

13. The pressure reactor of claim 12, wherein said pipeline extends in said container beyond said heating zone and into said tapered lower sector of said container.

14. The pressure reactor of claim 12, wherein said outlet flow regulation means comprise a drain pipe connected to said outlet opening of said outlet means and through which the liquid flows, and a flow control device connected to said drain pipe for regulating the flow of the liquid from said drain pipe.

15. The pressure reactor of claim 11 further comprising means arranged in said interior space of said container for monitoring the level of the liquid released from said pipeline into said interior space of said container.

16. Process for carrying out wet chemical reactions comprising the steps of:
   pressurizing an interior space of a pressure container,
   mixing a portion consisting of liquids or suspensions with a regent to form a reaction mix to be subjected to the wet chemical reaction,
   conveying the reaction mixture into the container,
   generating a microwave field in the container,
   passing the reaction mixture in a microwave-transparent part of a pipeline through the microwave field effective in the container such that the reaction mixture is heated while in the microwave-transparent part of the pipeline, to effect the wet chemical reaction and form a reaction product
   releasing the reaction product after it has been heated into the interior space of the container, and
   removing the reaction product from the container through an outlet opening therein.

17. Process for sterilizing liquids, comprising the steps of:
   pressurizing an interior space of a pressure container,
   continuously pumping liquid to be sterilized to the container,
   generating a microwave field in the container,
   passing the liquid in a microwave-transparent segment of a pipeline through the microwave field effective in the container such that the liquid is heated while in the microwave-transparent segment of the pipeline,
   releasing the liquid after it has been heated and thus sterilized into the interior space of the container, and
   removing the sterilized liquid from the container through an outlet opening therein.

18. The process of claim 17, further comprising the step of cooling the liquid after it has been heated and before it has been removed from the container.

19. The pressure reactor of claim 1, wherein the pressure in said pipeline is substantially equal to the pressure to which said interior space of said container is pressurized by said container pressurizing means.

20. A microwave-heatable pressure reactor for heating liquids, comprising a container having a pressurizable interior space, at least a part of said container comprising microwave-transparent material;

means coupled to said container for pressurizing said interior space of said container;

microwave heating means for generating a microwave field to be effective through said microwave-transparent part of said container to provide a heating zone in said interior space of said container;

a pipeline for conveying a liquid from a source thereof into and at least partially through said container, at least a part of said pipeline situated in said container comprising microwave-transparent material and being arranged in said heating zone, said pipeline having an outlet opening situated in said container through which the liquid is released into said interior space of said container; and means for pumping the liquid from the source through the pipeline to the container; and outlet means coupled to said container for removing liquid from said interior space of said container.

* * * * *